(12) United States Patent
Järverud et al.

(10) Patent No.: US 8,068,908 B2
(45) Date of Patent: *Nov. 29, 2011

(54) IMPLANTABLE CARDIAC STIMULATOR, SYSTEM, DEVICE AND METHOD FOR MONITORING CARDIAC SYNCHRONY

(75) Inventors: Karin Järverud, Solna (SE); Kenth Nilsson, Åkersberga (SE); Sven-Erik Hedberg, Kungsängen (SE)

(73) Assignee: St. Jude Medical AB, Jarfalla (SE)

( * ) Notice: Subject to any disclaimer, the term of this patent is extended or adjusted under 35 U.S.C. 154(b) by 580 days.

This patent is subject to a terminal disclaimer.

(21) Appl. No.: 12/094,543

(22) PCT Filed: Nov. 30, 2005

(86) PCT No.: PCT/SE2005/001806
§ 371 (c)(1),
(2), (4) Date: May 21, 2008

(87) PCT Pub. No.: WO2007/064259
PCT Pub. Date: Jun. 7, 2007

(65) Prior Publication Data
US 2008/0294216 A1    Nov. 27, 2008

(51) Int. Cl.
*A61N 1/00* (2006.01)
(52) U.S. Cl. .......................................................... 607/9
(58) Field of Classification Search .................. 600/437, 600/445, 481, 508, 509, 536; 607/9, 17, 607/18, 19
See application file for complete search history.

(56) References Cited

U.S. PATENT DOCUMENTS

| | | | |
|---|---|---|---|
| 5,427,112 A | 6/1995 | Noren et al. | |
| 5,556,419 A | 9/1996 | Jarverud et al. | |
| 5,628,777 A | 5/1997 | Moberg et al. | |
| 6,795,732 B2 | 9/2004 | Stadler et al. | |
| 2001/0012953 A1 | 8/2001 | Molin et al. | |
| 2002/0032386 A1* | 3/2002 | Sackner et al. | 600/536 |
| 2002/0143368 A1 | 10/2002 | Bakels et al. | |
| 2003/0105496 A1 | 6/2003 | Yu et al. | |
| 2004/0049112 A1* | 3/2004 | Yu et al. | 600/481 |
| 2004/0172079 A1 | 9/2004 | Chinchoy | |
| 2005/0209649 A1 | 9/2005 | Ferek-petric | |
| 2006/0178586 A1* | 8/2006 | Dobak | 600/508 |
| 2008/0255629 A1* | 10/2008 | Jenson et al. | 607/19 |
| 2010/0222836 A1* | 9/2010 | Jarverud | 607/17 |

* cited by examiner

*Primary Examiner* — George Manuel
*Assistant Examiner* — Robert Wieland
(74) *Attorney, Agent, or Firm* — Schiff Hardin LLP

(57) ABSTRACT

In a system and method for monitoring cardiac synchrony in a human heart, a first sensor is positioned at a first cardiac wall location of a heart that is subject to movements related to longitudinal valve plane movements along the longitudinal axis of the heart, and the first sensor measures said cardiac wall movements at the first cardiac wall location and emits a first sensor output signal corresponding thereto, a second sensor is positioned at a second cardiac wall location of the heart that is subject to movements related to longitudinal valve plane movements along the longitudinal axis of the heart, and the second sensor measures the cardiac wall movements at the second cardiac wall location and emits a second sensor output signal corresponding thereto. A lead arrangement is electrically connected to the first and second sensors and conducts the first and second sensor output signals therefrom to processing circuitry that processes the first and second sensor output signals to produce a synchronization signal therefrom indicative of synchrony in the respective valve plane movements at the first and second cardiac wall locations.

42 Claims, 8 Drawing Sheets

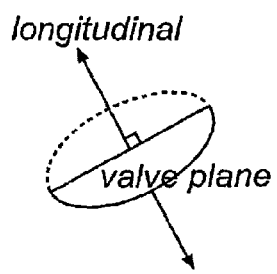 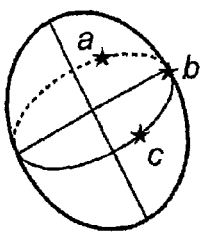 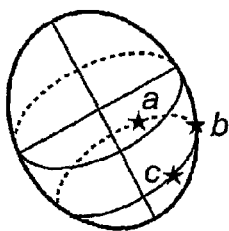 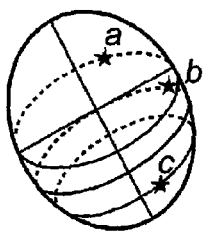
Fig. 9a    Fig. 9b    Fig. 9c    Fig. 9d
 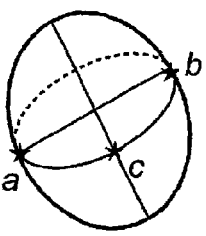 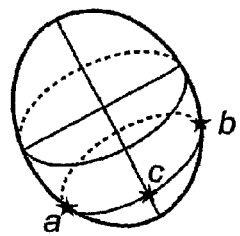 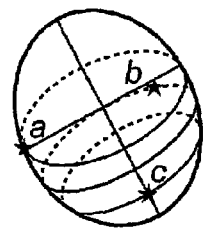
Fig. 10a    Fig. 10b    Fig. 10c    Fig. 10d

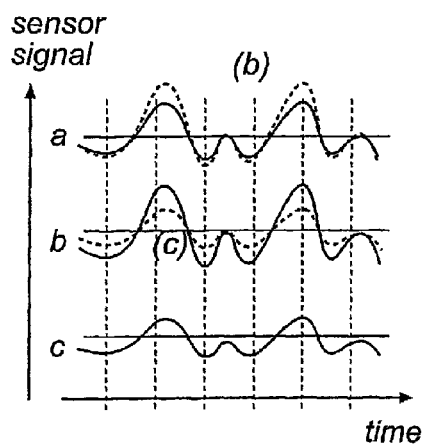 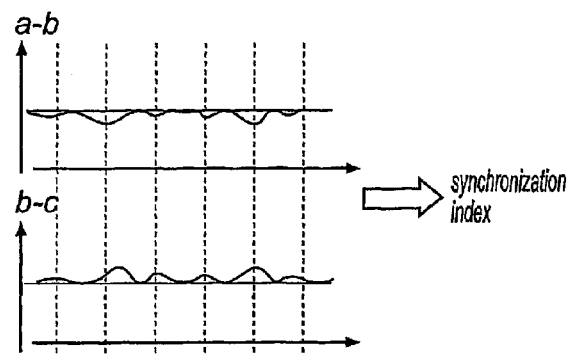
Fig. 11a  Fig. 11b
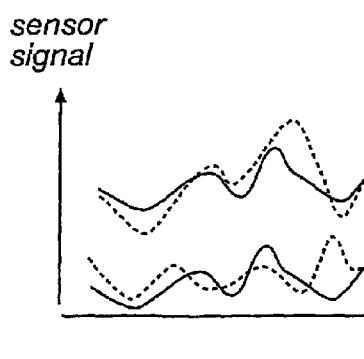 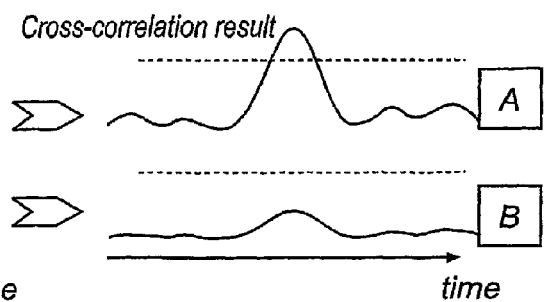
Fig. 12a  Fig. 12b

IMPLANTABLE CARDIAC STIMULATOR, SYSTEM, DEVICE AND METHOD FOR MONITORING CARDIAC SYNCHRONY

BACKGROUND OF THE INVENTION

1. Field of the Invention

The present invention generally relates to the field of implantable heart stimulation devices, such as pacemakers, implantable cardioverter-defibrillators (ICD), and similar cardiac stimulation devices that also are capable of monitoring and detecting electrical activities and events within the heart. More specifically, the present invention relates to a device for monitoring cardiac synchrony in a human heart, a system including such a device, an implantable cardiac stimulator comprising such a system, and a method of determining cardiac synchrony in a human heart.

2. Description of the Prior Art

Implantable heart stimulators that provide stimulation pulses to selected locations in the heart, e.g. selected chambers, have been developed for the treatment of cardiac diseases and dysfunctions. Heart stimulators have also been developed that affect the manner and degree to which the heart chambers contract during a cardiac cycle in order to promote the efficient pumping of blood. The heart will pump more effectively when a coordinated contraction of both atria and both ventricles can be provided.

In a healthy heart, the coordinated contraction is provided through conduction pathways in both the atria and the ventricles that enable a very rapid conduction of electrical signals to contractile tissue throughout the myocardium to effectuate the atrial and ventricular contractions. If these conduction pathways do not function properly, a slight or severe delay in the propagation of electrical pulses may arise, causing asynchronous contraction of the ventricles which would greatly diminish the pumping efficiency of the heart. Patients who exhibit pathology of these conduction pathways, such as patients with bundle branch blocks, etc., can thus suffer compromised pumping performance.

Various prior art procedures have been developed for addressing these and other disorders. For instance, cardiac resynchronization therapy (CRT) can be used for effectuating synchronous atrial and/or ventricular contractions. Furthermore, cardiac stimulators may be provided that deliver stimulation pulses at several locations in the heart simultaneously, such as biventricular stimulators. The stimulation pulses could also be delivered to different locations with a selected delay in an attempt to optimize the hemodynamic performance, e.g. maximize cardiac output, in relation to the specific cardiac dysfunction present at the time of implant.

However, even though ventricular and atrial synchrony may be present at the time of implant, possibly supported by suitable cardiac stimulation therapy, this may not necessarily be the case at a later stage. For instance, during progression of cardiac therapy after implantation of a cardiac stimulator, the cardiac tissue may adapt itself to the new conditions. Then, the function of hibernating myocardial tissue may be at least partially restored, and the overall cardiac function may become different from that at the time of implant.

In other words, ventricular and atrial synchrony from the time of implant may turn into asynchrony at a later stage, possibly supported or induced by stimulation therapy, as a result of a local improvement in the local function of myocardial tissue. For instance, the functions of myocardial portions or regions that at the time of implant were affected by slow conduction or post-systolic contractions (PSC), could at a later stage have improved their behavior such that there is no longer any slow conduction or PSC, or the PSC patterns have changed. Thus, even though there is an improvement in the behavior of myocardial tissue through the remodulation or recovery of the heart during progression of cardiac therapy, there may be an impairment in the overall function of the heart since the pacing therapy is not adapted to the new situation. During follow-up, a physician may alter the delay settings in adaptation to altered cardiac status. However, a need still exists for monitoring changes in ventricular and/or atrial synchrony in the heart of a patient.

SUMMARY OF THE INVENTION

An object of the present invention is to provide a new solution for monitoring cardiac synchrony of a human heart.

According to one aspect of the present invention, this object is achieved by a device for monitoring cardiac synchrony in a human heart, the device being connectable to a first sensor and a second sensor respectively adapted to be positioned at a first cardiac wall location and a second cardiac wall location that are subject to movements related to longitudinal valve plane movements along the longitudinal axis of the heart. The first and second sensors are arranged for measuring cardiac wall movements at the first and second cardiac wall locations, respectively. The device has processing circuitry arranged for receiving output signals from the first and second sensors, the output signals being respectively indicative of said longitudinal valve plane movements at the respective cardiac wall locations. The processing circuitry is configured to process the output signals and provide a synchronization signal indicative of the synchrony in the valve plane movements at the first and second cardiac wall locations.

The above object also is achieved according to another aspect of the present invention by a system for monitoring cardiac synchrony in a human heart. The system has a first sensor adapted to be positioned at a first cardiac wall location that is subject to movements related to longitudinal valve plane movements along the longitudinal axis of the heart. The first sensor is arranged for measuring cardiac wall movements at the first cardiac wall location, and a second sensor is adapted to be positioned at a second cardiac wall location that is subject to movements related to longitudinal valve plane movements along the longitudinal axis of the heart. The second sensor is arranged for measuring cardiac wall movements at the second cardiac wall location. The system further has a device for monitoring cardiac synchrony in a human heart as described above.

According to yet another aspect of the present invention, an implantable cardiac stimulator for delivering stimulation pulses to a human heart has a housing, a pulse generator enclosed in the housing for generating said stimulation pulses, control circuitry for controlling the delivery of the stimulation pulses to the heart, and a device for determining cardiac synchrony in a human heart as described above. The stimulator is connectable to a lead arrangement for conducting said stimulation pulses to the heart, and for conducting electrical signals from the heart to the control circuitry. It is to be noted that the term "implantable cardiac stimulator" is intended to encompass any implantable device arranged for providing electrical stimuli for controlling the operation of a human heart, such as an ICD or a pacemaker, e.g. of biventricular, dual-chamber, AV-sequential, or any other type known in the art.

According to a further aspect of the present invention, there is provided a method of determining cardiac synchrony in a human heart. The method includes the steps of sensing first cardiac wall movements at a first location subjected to movements related to longitudinal valve plane movements along the longitudinal axis of the heart, sensing second cardiac wall movements at a second location subjected to movements related to the longitudinal valve plane movements, and providing a synchronization signal based on the sensed first and second cardiac wall movements, the synchronization signal being indicative of the synchrony in the valve plane movements at the first and second locations.

According to a still further aspect of the present invention, there is provided a method of controlling the delivery of stimulation pulses to a human heart. The method includes the steps of generating stimulation pulses, controlling parameters for the timing of stimulation pulse delivery to the heart, delivering the stimulation pulses to the heart, sensing first cardiac wall movements at a first location subjected to movements related to longitudinal valve plane movements along the longitudinal axis of the heart, sensing second cardiac wall movements at a second location subjected to movements related to the longitudinal valve plane movements, and providing a synchronization signal based on the sensed first and second cardiac wall movements, the synchronization signal being indicative of the synchrony in the valve plane movements at the first and second locations.

The present invention is based on the advantageous idea of monitoring the longitudinal movements of the valve-plane in order for determining cardiac synchrony in a human heart. A detected asynchrony in the longitudinal valve plane movement can be an indicator of an impaired cardiac function. Such an impairment can be related to ischemic heart disease, congestive heart failure, diastolic and/or systolic dysfunction, etc. Studies have shown that the valve plane of the heart in a healthy individual moves longitudinally during the heart cycle. Simply put, ventricular contraction pulls the valve plane downwards, while ventricular relaxation moves the valve plane upwards. Furthermore, the movement of the valve plane in a healthy individual is essentially synchronous, while an asynchronous movement of the valve plane, e.g. a tilt in the valve plane movements, can be regarded as a strong indicator for an impaired cardiac function. Examples thereof can be found in "Left ventricular long axis function in diastolic heart failure is reduced in both diastole and systole: time for a redefinition", G Yip et al., Heart 2002; 87:121 125.

It should be noted that the cardiac synchrony in the longitudinal movements of the valve-plane could be related to synchrony during the systolic phase of the heart cycle, synchrony during the diastolic phase of the heart cycle, or synchrony of the overall heart cycle. The cardiac synchrony could also be determined for a shorter portion of the cardiac cycle, such as during the QRS-complex or the T-phase.

As stated above, a cardiac asynchrony result in a compromised pumping performance of the heart. Thus, one effect of maintaining or even improving the cardiac synchrony of the heart cycle, in particular during the systolic phase, is that the cardiac output may be maintained at a desired level, or even improved. Usually, an improvement in the cardiac output of a patient, i.e. the volume of blood ejected by the heart per minute, results in an improvement in the overall wellbeing of the patient.

Furthermore, it should in this context also be noted that the synchronization of myocardial relaxation during the diastolic phase of the heart cycle is beneficial for maintaining coronary flow at a desired level. All coronary blood supply, or cardiac perfusion, occurs during the diastolic phase of the heart cycle, i.e. when the myocardium relaxes between contractions. At the onset of the systolic phase, the myocardial tissue is contracted, thereby also contracting the coronary arteries and arterioles such that coronary flow virtually comes to a stop during systole. When the myocardial tissue relaxes and dilates, the arteries and arterioles also become dilated and the pressure gradient built up during the systolic phase forces the flow of blood through the coronary arteries and veins. Thus, the diastolic phase should be sufficiently long and undisturbed for providing sufficient time for coronary flow to occur.

Moreover, the term "valve-plane" refers to the annulus fibrosis plane separating the ventricles from the atria and containing all four heart valves, i.e. the aortic, pulmonary, mitral, and tricuspid valves. The term "longitudinal axis of the heart" or "long-axis of the heart" refers to a direction of the heart which is substantially perpendicular to the valve plane.

Thus, according to the invention, longitudinal movements of the valve plane are measured at a plurality of locations in the heart, for the purpose of monitoring cardiac synchrony. At each location, a sensor is provided for sensing and measuring longitudinal cardiac wall movements at the location of the sensor. The sensor generates an output signal which is indicative of the sensed cardiac wall movements. Preferably, the output signals provide an indication of both the timing of the cardiac wall movements, and the magnitudes thereof. Furthermore, the sensors could be arranged to provide output signals indicative also of the directions of the cardiac wall movements. However, this is not a prerequisite for monitoring cardiac synchrony.

The output signals from the respective sensor are compared to one another, and a resulting comparison signal may be processed in order to arrive at a synchronization signal or index. Thereby, a level of synchrony in the longitudinal valve plane movements may be determined, which can be used as an indication of whether the applied cardiac stimulation therapy needs adjustment.

According to the present invention, only longitudinal valve plane movements are measured for monitoring the synchrony in a human heart. Thus, the sensors may according to some embodiments be arranged to provide output signals which are substantially only indicative of movements related to the longitudinal movements of the valve plane. This can be achieved in a number of different ways. In one example, use can be made of sensors which are sensitive for one direction component of the movements only. The sensor could then be positioned and oriented such that the so called sensitive direction of the sensor is oriented in parallel to the longitudinal direction of the valve plane movements. In another example, the sensor could be positioned at a location in which the cardiac wall moves substantially only in the longitudinal direction of the valve plane. Such a location could be in the actual valve plane, for instance using an epicardial sensor attached to the epicardium of the human heart. Another location could be in the epicardium or the endocardium in the vicinity of the valve plane.

Furthermore, the processing circuitry could be arranged for discriminating longitudinal cardiac wall movements, i.e. parallel to the longitudinal valve plane movements, from lateral movements in an output signal from a sensor that is sensitive to movements in both the longitudinal and the lateral directions. The term "lateral movements" refers in this context to movements of the cardiac wall that is perpendicular to the longitudinal direction. Accordingly, a radial movement will herein be referred to as a lateral movement. It should in this context be noted that during the systolic and diastolic phases of a heart cycle, almost every cardiac wall portion of the heart will be moved due to the contractions and relaxations of the ventricles and atria. Likewise, there will be a longitudinal direction component in the cardiac wall movements for almost all locations. Thus, the processing circuitry could be arranged for extracting the relevant longitudinal movement information from an aggregate signal. However, use is preferably made of sensors having directions of sensitivity which is weighted towards movements in the longitudinal axis of the heart such that the output signal thereof presents a significantly larger longitudinal than lateral direction component, or provided at a location subjected to significantly larger longitudinal than lateral movements during the heart cycle.

It should be noted that a number of different sensors could be used in the context of this invention for sensing cardiac wall movements, which are known to those skilled in the art. For example, the sensors could be in the form of accelerometers, of any suitable type, or in the form of piezoelectric pressure transducers. Thus, the scope of the present invention is not restricted to the particular sensor alternatives disclosed herein.

Furthermore, according to exemplifying embodiments, different types of sensors for sensing or measuring cardiac wall movements may be used with the same cardiac stimulator. Thus, at least one sensor can be an accelerometer while at least one other sensor is a pressure sensor. Then, the output signals from the different types of sensors, respectively, are analyzed and compared to each other with regards to shape, timing and coherency.

According to embodiments of the present invention, two sensors may be used for determining cardiac synchrony. However, any number of sensors are contemplated within the scope of the present invention. Since the cardiac wall movements measured by the sensors are to a certain extent dependent on the actual location of the sensor, the determined level of synchrony may be limited to a certain portion of the heart. Thus, if only two sensors are used, there may be a possibility of asynchronous behavior of the myocardium, or relevant portions thereof, not being detected by these two sensors. Thus, providing more than two sensors that are positioned at suitable spaced locations may increase the reliability of the synchronicity monitoring. However, this must of course be weighed against the possible trauma resulting from implantation of further sensors, as well as possible congestion in the veins in which possible implantable leads may be positioned. Consequently, the present invention is not restricted to the use of a specific number of cardiac wall movement sensors, even though specific examples and embodiments presented below may relate to the use of two or three sensors.

In exemplifying embodiments of the present invention, the synchronization monitoring is based on the output of two sensors, in which a first sensor is positioned at a location related to the right ventricle of the heart and arranged for sensing cardiac wall movements of the right ventricle, and the second sensor is positioned at a location related to the left ventricle of the heart and arranged for sensing cardiac wall movements of the left ventricle. Preferably, the right ventricle sensor is positioned within the right ventricle and attached to the ventricular wall, and the left ventricle sensor is positioned in the coronary sinus region outside the left ventricle and in contact with the left ventricular wall. In this example, interventricular or V V synchronization may be monitored. As used herein, the phrase "coronary sinus region" refers to the vasculature of the left ventricle, including any portion of the coronary sinus, great cardiac vein, left marginal vein, left lateral vein, left posterior ventricular vein, middle cardiac vein, and/or small cardiac vein or any other cardiac vein accessible via the coronary sinus.

In further exemplifying embodiments of the present invention, the synchronization monitoring is based on the output of two sensors positioned in or at the same ventricle. Then, the sensors are suitably used for monitoring synchronization within the same ventricle, i.e. for the right or the left ventricle. However, if one sensor is positioned within the right ventricle and attached to the cardiac septum, or in the immediate vicinity thereof, the sensor could be arranged to sense cardiac wall movements related to myocardial wall movements related to contractions originating from the left ventricle.

Moreover, one or more additional sensors could in further examples of the invention be provided in or at the left or the right ventricle for providing additional output signal(s) on which the synchronization monitoring is based. Also, sensors could be provided in the atrium for delivering output signal(s) on which the synchronization is based.

In some embodiments of the invention, all sensors for measuring cardiac wall movements are positioned in the valve plane, or in a plane parallel thereto. Then, an asynchrony in the movements of the cardiac wall portions, related to the longitudinal movements of the valve plane, between the sensor locations can very easily be determined and interpreted as an asynchrony in the overall longitudinal movements of the valve plane.

In other embodiments of the invention, the sensors may be positioned at locations related to cardiac wall regions of interest. These locations can be positioned in a plane parallel to the valve plane, but it is more likely that they will not. The regions of interest can be determined by the physician and for instance refer to regions which are considered to be susceptible to post-systolic contractions (PSC), or have slow conduction pathways. A further example of a region of interest could be a region having hibernating tissue expected to recover during progression of cardiac therapy, which could change cardiac function and require adjustment of pacing or stimulation therapy parameters.

According to the present invention, a synchronization signal can be derived, preferably using processing circuitry provided in a cardiac stimulator, on the basis of the output signals from the respective sensors using a number of different methods, as understood by the person skilled in the art. According to one example, the synchronization index could be the actual difference in time for the sensed onset of longitudinal valve plane movements related to ventricular contraction experienced by the different sensors.

Furthermore, in accordance with another exemplifying embodiment, the difference between sensor output signals could be calculated, for instance by simply subtracting one output signal from another. The resulting difference signal could then be used as said synchronization signal per se, or statistical calculations could be applied to the difference signal to arrive at a suitable value indicative of the synchronization. If more than two sensors are used, a plurality of difference signals could be provided, for selected sensor combinations or for all combinations. The plural difference signals could then simply be aggregated to obtain a synchronization signal that would take into account all sensors, or be subject to suitable statistical calculations to arrive at a synchronization index.

In yet further examples, the synchronization index or signal could be obtained through plotting of the sensor output signals in x-y plots and detecting patterns between the plots, for instance by cross-correlation, neural network signal processing, or loop discrimination. Such loop discrimination is disclosed in U.S. Pat. Nos. 5,427,112 and 5,556,419, the teachings of which are incorporated herein by reference.

However, the present invention is not restricted to the examples of methods for calculating a synchronization index or signal presented herein. On the contrary, any suitable method for calculating a synchronization signal or index from the output signals of the sensors measuring longitudinal valve plane movements is contemplated within the scope of the present invention.

According to some embodiments of the present invention, a comparison is made between the obtained synchronization index or signal and a threshold value or signal, preferably by processing circuitry provided in an implantable cardiac stimulator. Then, the threshold value would be an indicator whether the cardiac synchrony lies within an acceptable range or not. In other words, as long as the synchronization index is within a selected range, as defined by one or more threshold values, a desired level of cardiac synchrony is considered to be enabled. However, should the synchronization index fall outside the intended range, an indication of cardiac asynchrony, or insufficient cardiac synchrony, may be provided.

Such an indication could in exemplifying embodiments of the invention be used for triggering a change in the stimulation or pacing therapy. Such a change could for example refer to an adjustment in the VV-interval, e.g. for a biventricular heart stimulator; a change in the AV-interval, e.g. for a dual chamber heart stimulator; or combinations thereof. Thereby, the cardiac synchrony can be monitored during remodulation of the patient's heart, and the stimulation or pacing therapy can be adjusted in adaptation to the remodulation of the heart.

In further embodiments, the indication of cardiac asynchrony could be used for triggering an alarm signal to the patient. This alarm signal could be intended for prompting the patient to seek medical assistance for care or follow-up.

It should be understood that the indication of cardiac asynchrony does not have to be a binary value. On the contrary, the asynchrony indication preferably also provides information of the severity of asynchrony. Thus, the threshold value as referred to above, may in fact be a number of threshold values. For instance, a first value could be an indication of slight asynchrony to be used for diagnostic purposes, a second value could trigger a change in the pacing therapy, and a third value could be used for triggering an alarm to the patient that he needs to see his/her physician.

The monitoring of cardiac synchrony and/or detection of cardiac asynchrony is preferably performed at predetermined time intervals. As an example, the monitoring could be performed by receiving the output signals from the sensors, and providing a synchronization signal once a week, every three days, once a day, every 8 hours, etc. Preferably, the time interval is set such that monitoring is performed often enough for a cardiac asynchrony to be detected at such an early stage that corrective action may be immediately taken and possible detrimental effects avoided, and seldom enough such that an unduly large energy consumption resulting from the monitoring procedure may be avoided.

In some embodiments, the time interval may be varied in adaptation to expected possible changes in the function of the heart. For instance, it may be expected that variations and changes in the myocardial function is most likely to occur, and to occur most frequently, in the time immediately following implantation. Thus, the monitoring interval can be set at a short interval for the period immediately following implant, and then be automatically extended as the time from implantation increases.

Furthermore, the time interval may be shortened as a result of detected changes in the cardiac synchrony. Thus, following a change in cardiac synchrony, possibly into asynchrony with ensuing corrective actions taking place, the time interval is suitably decreased in order to frequently monitor for possible further deterioration, or for an improvement as a result of the corrective actions taken.

Moreover, immediately following a change in the pacing therapy, determinations of possible asynchrony should take place. Also, if the synchronization signal or index is a quantitative value directly indicating the level of synchrony, the change in synchronization based on any pacing therapy variations can be monitored and the pacing therapy further adjusted accordingly.

In further examples, if the monitoring should indicate that cardiac asynchrony has arisen, then one or more further measurements and determinations of cardiac synchronization may be performed before an indication of asynchrony is provided and possible ensuing actions are initiated. Thereby, a sudden, isolated asynchronous event will not have an undue impact on the overall stimulation pacing therapy.

In the examples that will be presented in the following, the sensors are provided at the distal end of cardiac leads that are arranged for providing stimulation pulses to the atria and/or ventricles of the heart, or for conducting sensed intrinsic cardiac signals from the heart to the heart stimulator. However, it should be noted that sensors provided on separate implantable leads, or other implantable devices, are also contemplated in the context of this application. Thus, the scope of the present invention is not restricted to sensors arranged on such implantable leads for stimulation and sensing as will be discussed below.

Further objects and advantages of the present invention will be discussed below by means of exemplifying embodiments.

BRIEF DESCRIPTION OF THE DRAWINGS

FIGS. 6a-6c are schematic illustrations of the determination of synchrony according to embodiments of the present invention.

FIGS. 8a-8c illustrate the determination of an asynchrony resulting from a local post-systolic contraction in the diastolic phase.

FIGS. 9a-9d illustrate examples of sensor positions where all sensors are positioned at the left ventricle.

FIGS. 10a-10d illustrate examples of sensor positions where sensors are positioned at both the right and the left ventricle, respectively.

FIGS. 11a and 11b illustrate in diagram form a first example of how a synchronization index may be obtained.

FIGS. 12a and 12b illustrate in diagram form a second example of how a synchronization index may be obtained.

DESCRIPTION OF THE PREFERRED EMBODIMENTS

The following is a description of exemplifying embodiments in accordance with the present invention. This description is not to be taken in a limiting sense, but is made merely for the purpose of describing the general principles of the invention. Thus, although particular types of heart stimulators will be described, such as biventricular pacemakers with or without atrial sensing and/or stimulation, the invention is also applicable to other types of cardiac stimulators, such as univentricular or dual chamber pacemakers, implantable cardioverter defibrillators (ICD's), etc.

Figure 1:
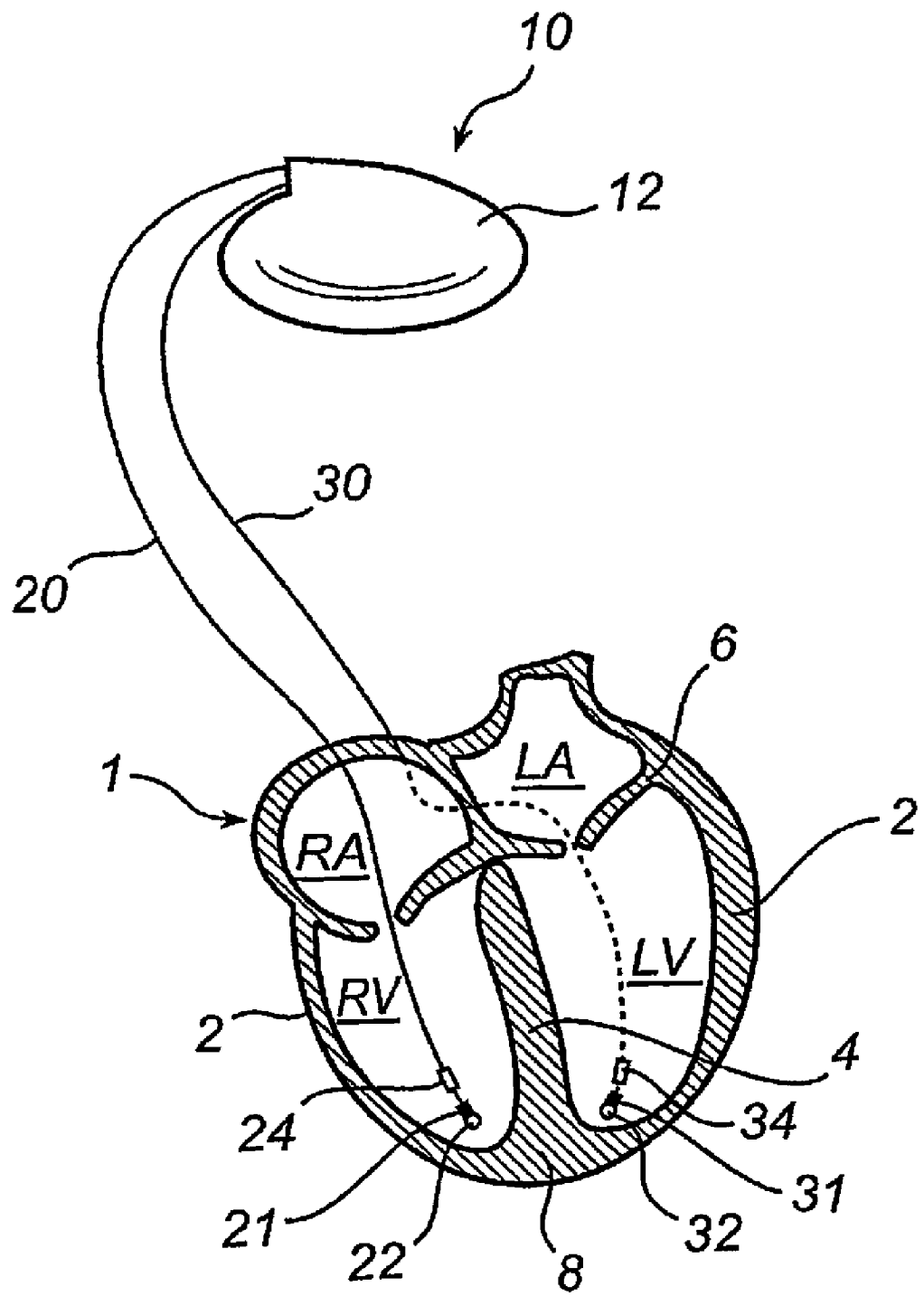
FIG. 1 is a simplified, partly cutaway view illustrating an implantable stimulator according to one exemplifying embodiment of the present invention.

With reference first to FIG. 1, there is shown a stimulation device 10 in electrical communication with a patient's heart 1 via two leads 20 and 30 suitable for delivering multi-chamber stimulation (and possible shock therapy). The heart illustrated portions of the heart 1 include the right atrium RA, the right ventricle RV, the left atrium LA, the left ventricle LV, cardiac walls 2, the ventricular septum 4, the valve plane 6, and the apex 8. The valve plane 6 refers to the annulus fibrosis plane separating the ventricles from the atria and containing all four heart valves, i.e. the aortic, pulmonary, mitral, and tricuspid valves.

In order to sense right ventricular cardiac signals and to provide stimulation therapy to the right ventricle RV, the stimulation device 10 is coupled to an implantable right ventricular lead 20 having a ventricular tip electrode 22, a ventricular annular or ring electrode 24, and a cardiac wall movement sensor 21. The ring electrode 24 is arranged for sensing electrical activity, intrinsic or evoked, in the right ventricle RV. The right ventricular tip electrode 22 is arranged to be implanted in the endocardium of the right ventricle, e.g. near the apex 8 of the heart. Thereby, the tip electrode 22 becomes attached to the cardiac wall and follows the cardiac wall movements, which movements can be sensed by the sensor 21 arranged near the tip electrode. In this example, the sensor is fixedly mounted in a distal header portion of the lead 20, in which the tip electrode 22 is also fixedly mounted. Furthermore in this example, the sensor is in the form of an accelerometer. However, other arrangements sensor types are contemplated for the cardiac wall motion sensor 21.

In order to sense left ventricular cardiac signals and to provide pacing therapy for the left ventricle LV, the stimulation device 10 is coupled to a "coronary sinus" lead 30 designed for placement via the coronary sinus in veins located distally thereof, so as to place a distal electrode adjacent to the left ventricle. Also, additional electrode(s) (not shown) could thereby be positioned adjacent to the left atrium. The coronary sinus lead 30 is designed to receive ventricular cardiac signals from the cardiac stimulator 10 and to deliver left ventricular LV pacing therapy using at least a left ventricular tip electrode 32 to the heart 1. In the illustrated example the LV lead 30 comprises an annular ring electrode 34 for sensing electrical activity related to the left ventricle LV of the heart. Furthermore, a cardiac wall movement sensor 31 is arranged at the tip electrode 32 for sensing left ventricular LV cardiac wall movements.

Figure 2:
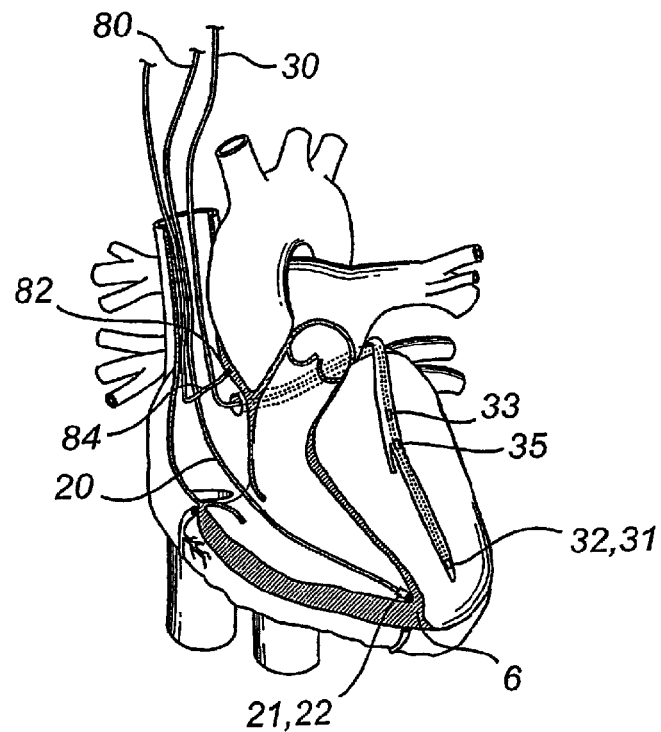
FIGS. 2 and 3 are partly cut-away views of a human heart provided with leads and sensors according to further exemplifying embodiments.
Figure 3:
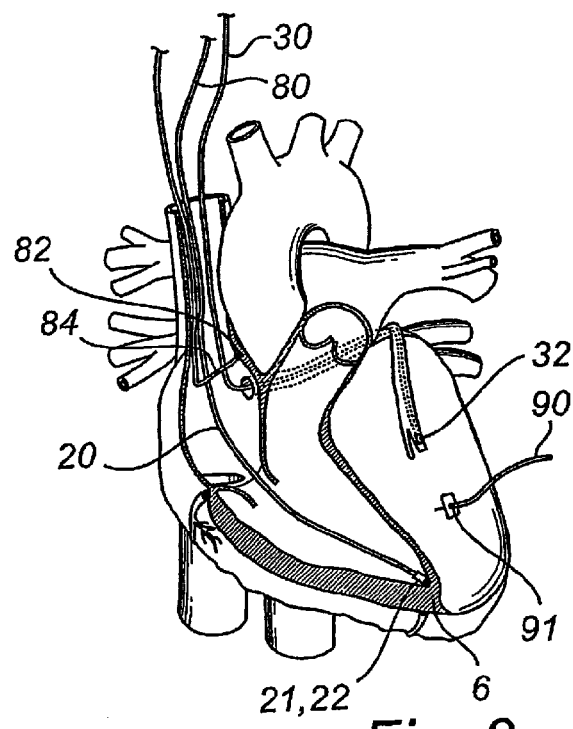

Turning briefly to FIGS. 2 and 3, two alternative embodiments for placement of cardiac leads, cardiac electrodes and sensors for sensing cardiac wall movements related to longitudinal valve plane movements are illustrated. In FIG. 2, the RV and LV leads 20, 30 have been supplemented with a right atrial RA lead 80. The lead comprises an RA tip electrode 82 positioned in the patient's right atrial appendage for delivering electrical stimuli to the right atrium, and an RA ring electrode 84 for sensing and conducting cardiac signals from the right atrium to the cardiac stimulator. A cardiac wall motion sensor is provided at the RA tip electrode 82 for sensing cardiac wall movements of the RA wall. Furthermore, the LV lead 30 is provided with an additional cardiac wall movement sensor 33 arranged at the valve plane 6, as well as an additional stimulating electrode, of the ring type, arranged distally of the movement sensor 33. Thereby, cardiac wall movements related to longitudinal valve plane movements at a plurality of locations, i.e. three or four, may be sensed and conducted via the cardiac leads 20, 30, 80 to the cardiac stimulator.

Furthermore, FIG. 3 illustrates yet another example of lead, electrode and sensor placements. Here, the RV, RA and LV leads 20, 30 and 80 have been supplemented by an external epicardial lead 90 connected to the implantable stimulator 10. The epicardial lead 90 may be arranged for delivering stimulation pulses to the left ventricle LV of the heart, but is in this example only arranged for sensing cardiac wall movements related to longitudinal valve plane movements and comprises a cardiac wall motion sensor 91. Thus, even though the LV lead 30 terminates and the stimulation electrode 32 for stimulation of the left ventricle arranged at a position near the valve plane 6 of the heart, local wall movements occurring in the LV cardiac wall further down towards the apex 8 may still be sensed.

Although three examples have been illustrated in FIGS. 1-3, the invention is not restricted to the illustrated examples of lead, electrode and sensor placement. For example, several epicardial electrodes and/or wall motion sensors could be used, wall motion sensors could be arranged at plural positions in the ventricles only, all wall motion sensors could be arranged in the same ventricle, plural atrial wall sensors could be used, etc. Also, in the illustrated examples, the wall motion sensors are of accelerometer type. However, other types of sensors for sensing and measuring wall movements related to longitudinal valve plane movements are to be comprised in the scope of the present application. Further examples of sensor placements will be presented in relation to the further embodiments that will be described below.

Figure 4:
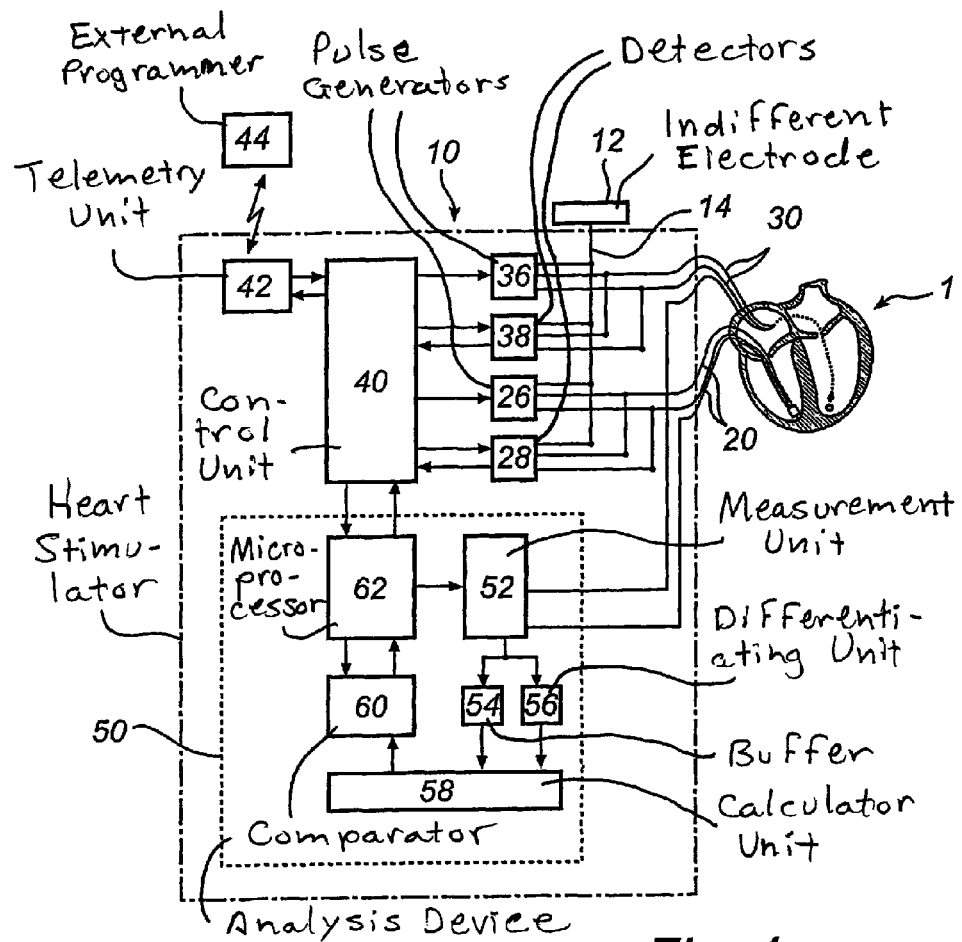
FIG. 4 is an illustration in a block diagram form of an implantable stimulator according to the embodiment shown in FIG. 1.

Turning now to FIG. 4, the heart stimulator 10 of FIG. 1 is shown in a block diagram form. For illustrative purposes, reference is made to FIG. 1 for the elements of the leads that are intended for positioning in or at the heart. The heart stimulator 10 is connected to a heart 1 in order to sense heart signals and emit stimulation pulses to the heart 1. A first tip electrode 22 is anchored in the right ventricle RV of the heart 1 and connected, via a first electrode conductor in the lead 20, to a first pulse generator 26 in the heart stimulator 2. A first ring electrode 24 is connected near the first tip electrode 22 and, via a second electrode conductor in the first lead 20, to the first pulse generator 26. A stimulation pulse to the right ventricle can be delivered to heart tissue by the first pulse generator via the first lead 20 and the first tip electrode 22. The stimulation pulse is then returned, via the first ring electrode 24 and the first lead 20, to the first pulse generator 26. Alternately, the stimulation pulse can be delivered via the first tip electrode 22 and an indifferent electrode 12 which, in this instance, consists of the enclosure of the heart stimulator 10 but can also consist of a separate electrode located somewhere in the body. The indifferent electrode 12 is connected to the first pulse generator 26 via an electrode conductor 14 in order to return stimulation pulses from the right ventricle. A first detector 28 is connected in parallel across the output terminal of the first pulse generator 26 in order to sense right ventricular activity in the heart.

In corresponding manner, a second tip electrode 32 is positioned in a vein distally of the coronary sinus and, thus, connected to the left ventricle LV of the heart 1, and, via a conductor in the second lead 30, to a second pulse generator 36. A second ring electrode 34 is located near the second tip electrode 32 and connected, via a further conductor in the second electrode lead 30, to the second pulse generator 36.

Delivery of a stimulation pulse to the ventricle can be bipolar via the second tip electrode 32 and the second ring electrode 34, or unipolar via the second tip electrode 32 and the indifferent electrode 12. A second detector 38 is connected in parallel across the output terminal of the second pulse generator 36 in order to sense left ventricular activity in the heart. The pulse generators 26 and 36 and the detectors 28 and 38 are controlled by a control unit 40 which regulates the stimulation pulses with respect to amplitude, duration and stimulation interval, the sensitivity of the detectors 28 and 38 etc.

A physician using an extracorporeal programmer 56 can, via a telemetry unit 54, communicate with the heart stimulator 10 and thereby obtain information on identified conditions and also reprogram the different functions of the heart stimulator 10.

FIG. 4 further shows a first embodiment of an analysis device. The analysis device 50 is connected via the first electrode lead 20 to a first cardiac wall motion sensor 21 for sensing cardiac wall movements related to longitudinal valve plane movements, and via the second electrode lead 30 to a second cardiac wall motion sensor 31 for sensing cardiac wall movements related to longitudinal valve plane movements. The analysis device 50 includes a measurement unit 52 which is capable of selectively receiving signals from any of the sensors, and which filters and amplifies the incoming signals in an appropriate manner.

The output signal from the measurement unit 52, which is proportional to the measurement signal, is then sent to a buffer 54 and to a differentiating circuit 56. Buffering is performed so that the differentiated signal is in phase with the proportional signal when they are sent to a calculator unit 58. The calculator unit 58 calculates a synchronization or synchrony value or signal based on the output signals from the respective sensors. The calculated synchronization signal 58 is sent to a comparator 60 for comparison with a threshold value, for instance indicative of when insufficient cardiac synchrony is present.

The output signal from the comparator comprises information of whether the synchronization signal passes the threshold value, or one of the threshold values for embodiments where a number of threshold values are utilized, and is forwarded to a microprocessor 62 which communicates with the control unit 40. If, e.g., an asynchrony is identified, the control device 40 can institute therapeutic treatment with stimulation pulses in order to restore cardiac synchrony. The microprocessor 62 further controls the measurement unit 52 with respect to the measurement signal to be sent to the analysis device 50 and can also control the comparator 60, for example for varying threshold values in response to altered pacing therapy or due to altered settings by the physician.

Figure 5:
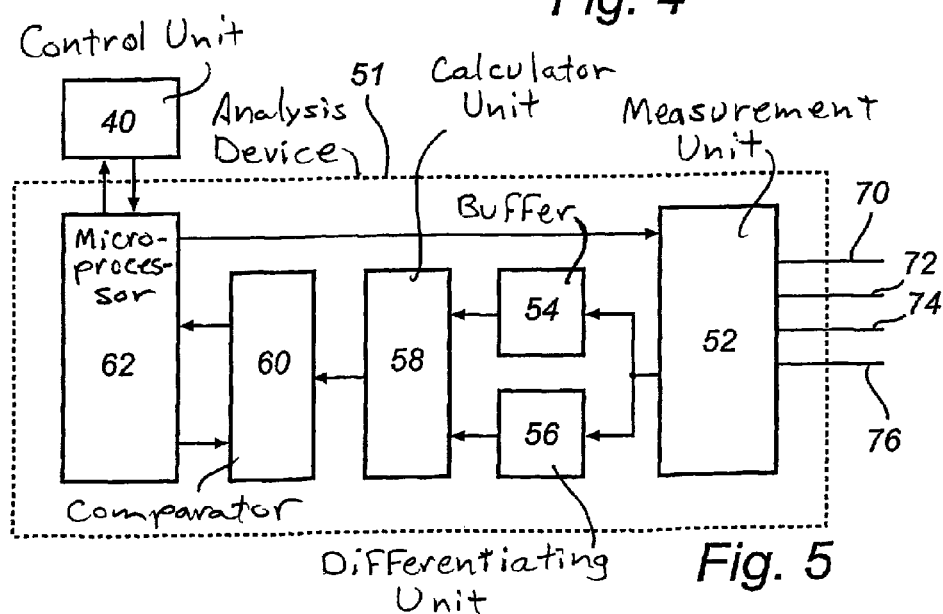

With reference now to FIG. 5, there is shown an alternative analysis device 51. This alternative analysis device 51 basically comprises the same or similar elements as described in relation to the measurement unit analysis device 50 of FIG. 4. However, the alternative analysis device 51 is arranged for receiving output signals from three cardiac wall motion sensors via conductors 70, 72 and 74, the analysis device thus being arranged to provide a synchronization signal indicative of cardiac synchrony between three different locations of the heart.

Furthermore, a fourth conductor 76 provides an IEGM signal for the measurement unit. The IEGM signal may provide an indication related to when the output signals of the sensors may be used for determining cardiac synchrony for a particular portion of the heart cycle. Thus, the IEGM signal may for instance be used by the analysis device 50, or rather by the differentiating circuit 54 and the calculator unit 58, as an aid in discriminating between the systolic and the diastolic phases of the heart cycle. Thereby, the analysis device can for instance be configured to process only sensor output signals provided during the diastolic phase. Then, there will be no risk of misinterpreting an asynchrony that may be present in the systolic phase as an asynchrony in the diastolic phase.

Turning now to FIGS. 6-6c and 7a-7c, there will be shown in schematic form the presence and determination of cardiac synchrony and asynchrony, respectively. In FIGS. 6a, 6b, 7a, and 7b, a heart is schematically illustrated with three cardiac wall motion sensors a, b and c positioned in the left ventricle LV of the heart.

In FIG. 6a, the position of the sensors, i.e. the cardiac wall portions in which the sensors are arranged, are illustrated at an instant when the myocardium is fully dilated, in particular during the diastolic phase of the heart cycle. Thus, the sensors and the wall portions thereof are in a respective position obtained from the longitudinal or long-axis valve plane movements as a result of myocardial relaxation. In FIG. 6b, an instant when the myocardium is at a state of myocardial contraction is illustrated, in particular during the systolic phase of the heart cycle. Thus, the movement of the sensors and the wall portions into the contracted positions have ceased and they are in a respective position obtained from the longitudinal valve plane movements as a result of myocardial contraction.

Figure 6C:
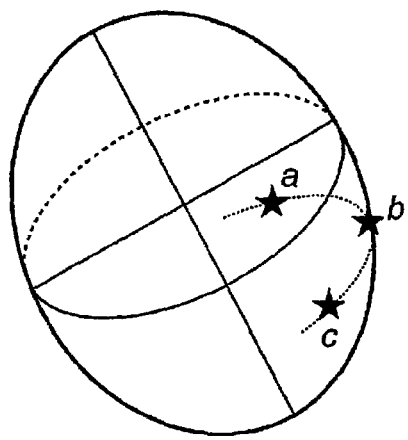
Figure 6C:
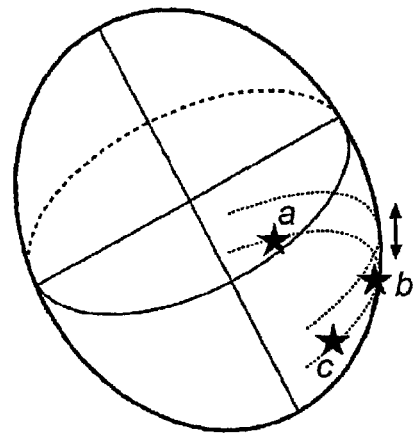
Figure 6C:
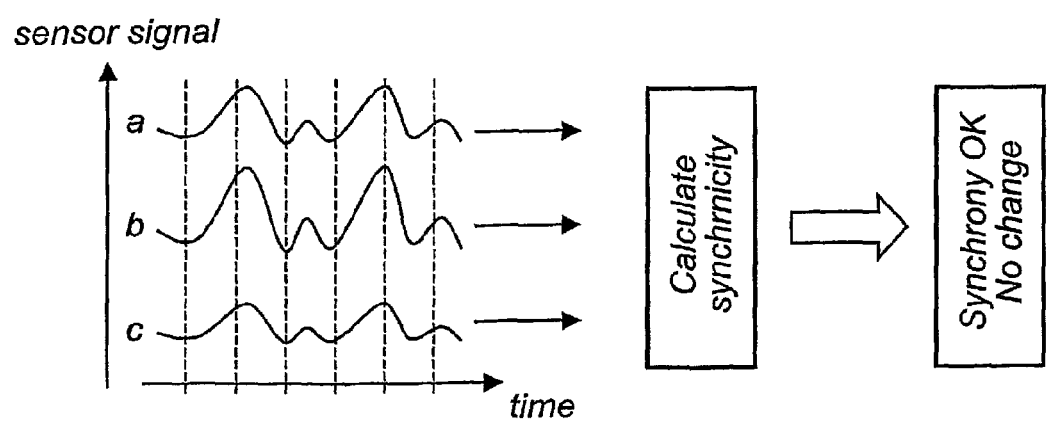

The output signals of the sensors are illustrated in FIG. 6c, and it can be seen that the movements sensed by the three sensors are substantially simultaneous throughout the heart cycle. Therefore, the processing circuitry, or analysis device, of the cardiac stimulator determines that there is cardiac synchrony. As a consequence, no further actions related to change in pacing therapy is performed. It should be noted that the determination of cardiac synchrony can be determined for the entire heart cycle, for the systolic phase, the diastolic phase, the transitions between diastolic and systolic phase, and vice versa, or any other time interval of the heart cycle that may be of particular interest for the determination of cardiac synchrony.

Figure 7A:
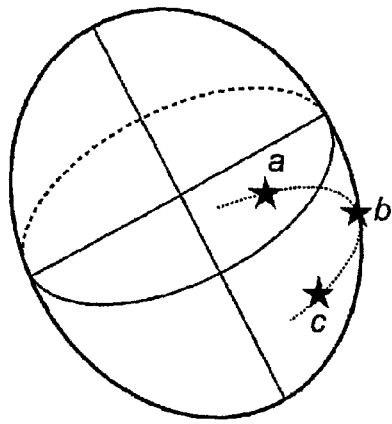
FIGS. 7a-7c are schematic illustrations corresponding to those of FIGS. 6a-6c, but in which an asynchrony is determined.
Figure 7B:
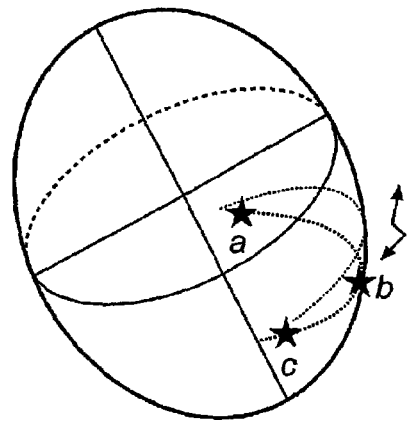
Figure 7C:
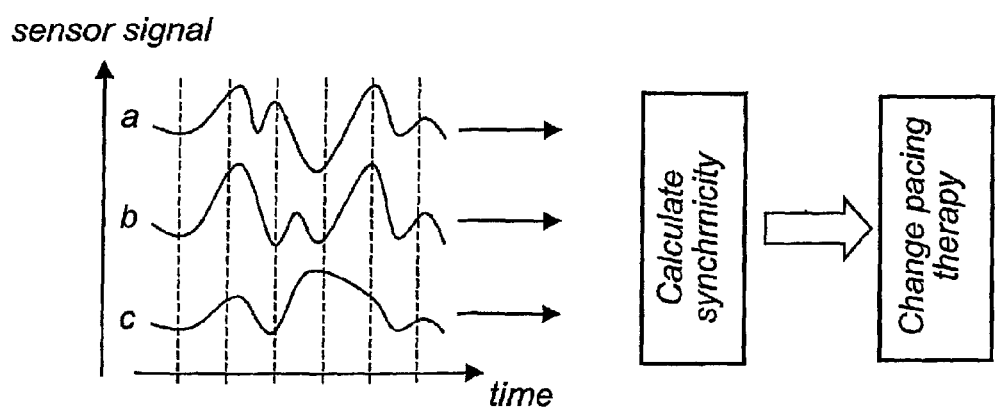

In FIG. 7a, the position of the sensors and the respective cardiac wall portions thereof correspond to that of FIG. 6a at an instant when the myocardium is fully dilated. Thus, the sensor positions are derived from the longitudinal valve plane movements resulting from myocardial relaxation. However, at the particular instant illustrated in FIG. 7b, only sensor b, and the cardiac wall portion to which sensor b is attached, has reached the position derived from the longitudinal valve plane movements obtained in the fully contracted state of the myocardium. Hence, there is lack in synchrony between the longitudinal valve plane movements for the cardiac wall portions at which the sensor a, b and c are attached, respectively. This lack in synchrony also appears in the output signals a, b and c of the cardiac wall motion sensors a, b and c, respectively. Thus, upon performing a synchronicity analysis for the output signals, for instance in the systolic phase of the heart cycle, it can be determined that cardiac asynchrony is present and that suitable measures should be taken. Such measures could include restoring the cardiac synchrony or to derive an alarm signal indicative of the cardiac asynchrony.

Figure 8C:
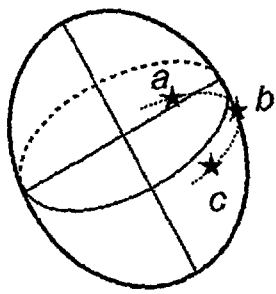
Figure 8C:
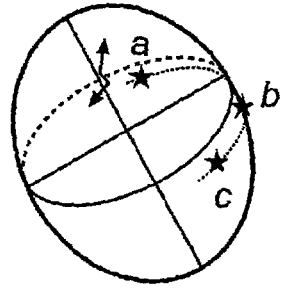
Figure 8C:
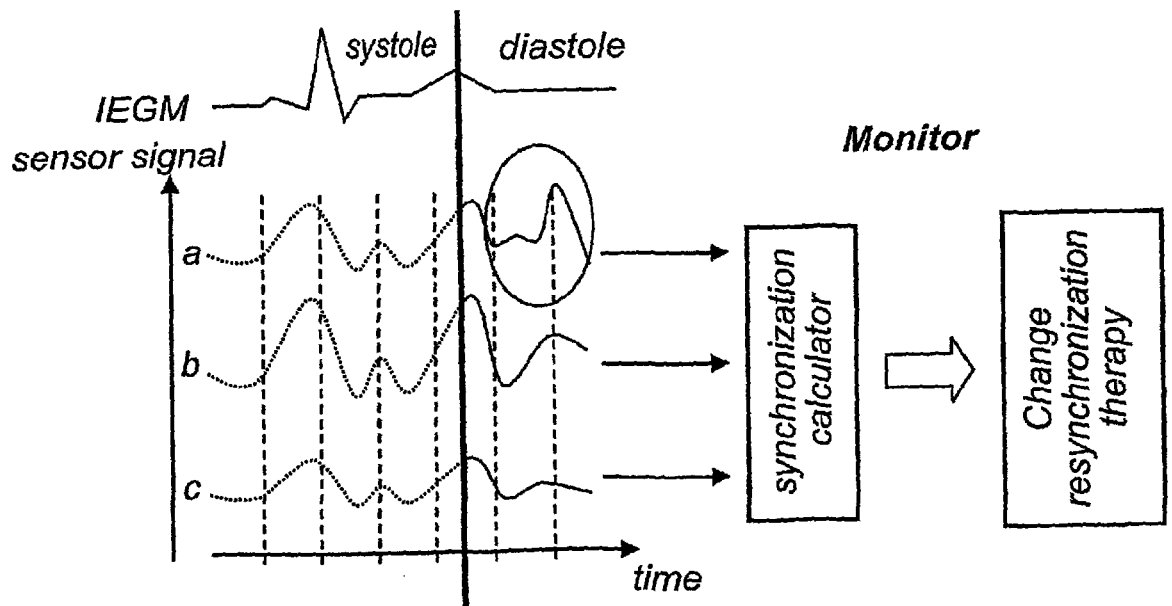

Turning now to FIGS. 8a-8c, there is shown a further example of the occurrence and detection of cardiac asynchrony related to longitudinal valve plane movements. In FIG. 8a, the positions of the cardiac wall motion sensors a, b and c at an instant where the myocardium has assumed a contracted state is shown. In FIG. 8b, a post-systolic contraction PSC occurs in the cardiac wall portion where sensor a is arranged for sensing cardiac wall movements derived from longitudinal valve plane movements. Consequently, sensor a is subjected to a longitudinal movement at an instant when sensors b and c remain substantially stationary during diastole. This appears in the combined sensor signal outputs a, b and c, and can be detected and determined as an asynchrony in the diastolic phase by the analysis device 50 of the stimulator 10. In the signal diagram of FIG. 8c, the portion comprising the signal output during the PSC is encircled. Thus, as a result of the determined asynchrony, appropriate adjustment of the pacing therapy may be executed in order to restore the cardiac synchrony.

In FIGS. 6a through 8b, substantially only one example of the positioning of cardiac wall motion sensors for sensing movements related to the longitudinal movements of the valve plane is provided. However, there are a vast number of sensor positioning alternatives that are contemplated within the scope of the present application. In fact, any placement of sensors for measuring cardiac wall motions occurring during the heart cycle may be used, as long as there is in fact movements of the particular portion to which the sensor is located and attached in relation to the longitudinal movements of the valve plane during the heart cycle, or any portion thereof. Thus, the present application is not limited to a particular number of wall motion sensors, or to particular positioning thereof.

Turning to FIGS. 9a-9d, further examples of wall motion sensors are provided. In these examples, the sensors a, b and c are arranged at the same ventricle, i.e. for measuring cardiac wall movements at several locations in the left ventricle LV of the heart. FIG. 9a is intended to illustrate the orientation of the valve plane, which is indicated by numeral 6 in FIG. 1. In the example illustrated in FIG. 9b, the sensors are positioned in the actual valve plane, which of course is suitable for detecting valve plane movements. Then, the sensors could in one alternative be positioned in the actual annulus fibrosis tissue, or epicardially outside the annulus fibrosis plane.

In FIGS. 9c and 9d, two alternative examples of sensor positionings are presented. In FIG. 9c, the sensors a, b and c have been positioned at equal distances from the valve plane, thus forming a sensor plane parallel to the valve plane. Thereby, the sensors are assumed to be subjected to movements related to the longitudinal valve plane movements of substantially the same distance during the heart cycle, which may be beneficial when calculating and determining synchrony and possible sudden or expected appearance of asynchrony in the valve plane movements.

In the example shown in FIG. 9d, the sensors are positioned at different levels at one ventricle along the longitudinal axis, or long-axis, of the heart. In this example, the physician has positioned the sensors at selected regions of interest, for instance regions suffering from a conductive disorder or having hibernating tissue which is expected or suspected to become active during remodulation of the heart due to progressing stimulation therapy.

Turning now to FIGS. 10a to 10d, further examples of sensor positioning are illustrated. In the examples, the sensors are arranged in or at both ventricles of the heart. First, FIG. 10a illustrates the valve plane and the longitudinal direction of the heart. Then, FIG. 10b illustrates the example where the cardiac wall motion sensors are positioned and arranged to sense longitudinal cardiac wall movements of the valve plane. The benefits thereof would of course be similar to the placement in the same ventricle as illustrated in FIG. 9b. Furthermore, in the same manner as mentioned above in relation to FIG. 9b, the sensors could in one alternative be positioned in the actual annulus fibrosis tissue, or epicardially outside the annulus fibrosis plane. Suitably, the right ventricular sensor a is arranged endocardially in the valve plane, and the left ventricular sensor c is arranged epicardially. The sensor b arranged at the septum 4 could be arranged epicardially either directly or via a coronary vein, or endocardially, via the right atrium and ventricle. Possibly, the RV sensor a arranged at the valve plane could be replaced for an RA sensor arranged in or at the valve plane, e.g. in the annulus fibrosis tissue.

In FIG. 10c, the sensors a, b and c have been positioned in or at the right and the left ventricle, respectively, at equal distances from the valve plane, thus forming a sensor plane parallel to the valve plane. Thereby, similar to the example shown in FIG. 9c, the sensors are assumed to be subjected to movements of substantially the same distance during the heart cycle, which may be beneficial when calculating and determining synchrony and possible sudden or expected appearance of asynchrony in the longitudinal valve plane movements.

In the example illustrated in FIG. 10d, the sensors are positioned at different levels, in or at the right and the left ventricle, along the longitudinal axis of the heart. In this example, similar to the example shown in FIG. 9d, the physician has positioned the sensors at selected regions of interest, for instance regions suffering from a conductive disorder or having hibernating tissue which is expected or suspected to become active during remodulation of the heart due to progressing stimulation therapy.

When the signal output from the sensors a, b and c is received by the analysis device 50, a calculation of a synchronization index or signal is performed, which can be used for determining synchrony of the heart. In FIG. 11a, the output signals a, b and c, stemming from the sensors a, b and c, respectively, indicative of cardiac wall movements are illustrated in a diagram. In the portion of the diagram illustrating sensor output signal a, the sensor output signal b has been added as shown by the dotted line. Similarly, the sensor output signal c has been added to the portion of the diagram illustrating sensor output signal b. In this example, the difference between the sensor output signals a and b and the difference between the sensor output signals is calculated. This is performed by simply subtracting sensor output signal b from a and sensor output signal c from b.

The resulting difference signals are shown in FIG. 11b. These signals could be further added to each other in order to arrive at the synchronization index or signal. Alternatively, the difference signals could be used separately in order to provide dual synchronization indices or signals. Furthermore, statistical calculations could be applied to the difference signal(s) to arrive at a suitable value indicative of the level of synchronization.

FIGS. 12a and 12b illustrate a further example of deriving one or more synchronization indices or signals. Here, the upper and lower portions of the diagram in FIG. 12a illustrates two signals obtained from two sensor output signals, respectively. One signal is indicated with a solid line, and the other one with a dotted line, respectively. These pairs of sensor output signals are cross-correlated in order to arrive at a cross-correlation result which is used as said synchronization indices or signals. In the illustrated example, two cross-correlation results in the form of synchronization index A and synchronization index B are obtained. The synchronization signals can then be compared with a threshold value, which is illustrated in FIG. 12b with the dotted straight line, and appropriate measures be taken when the synchronization signal exceeds the threshold level.

When the monitoring of cardiac synchronization has revealed that a cardiac asynchrony has arisen, or that a reduction of cardiac synchrony has occurred, the parameters for timing of stimulation pulse delivery may be changed in order to restore or improve the cardiac synchrony. Such an indication could in exemplifying embodiments of the invention be used for triggering a change in the stimulation therapy. Such a change could for example refer to an adjustment in the VV-interval, e.g. for a biventricular heart stimulator; a change in the AV-interval, e.g. for a dual chamber or an AV-sequential heart stimulator; or combinations thereof. Thereby, the cardiac synchrony can be monitored during remodulation of the patient's heart, and the pacing therapy can be adjusted in adaptation to the remodulation of the heart.

For heart stimulators in which the pacing therapy may be automatically adjusted by the heart stimulator in order to optimize or maximize cardiac output, a synchronized and elongated diastolic phase may be given priority over the optimization of cardiac output. For instance, in patients suffering from ischemic heart disease, it may be more important to ensure synchronized diastole and, thereby, adequate coronary flow at all times rather than maximized cardiac output.

In further embodiments, the indication of cardiac asynchrony could be used for triggering an alarm signal to the patient. This alarm signal could be intended for prompting the patient to seek medical assistance for care or follow-up.

It should be noted that the sensors may be subjected to pressures, movements and/or accelerations that are not derived from or related to the intrinsic movements of the myocardium and the cardiac walls thereof. For instance, accelerations derived from extra-cardiac movements of the patient, such as from running, vibrations in the patient environment, thoracic movements etc. However, output signal contributions deriving from intrinsic movements of the myocardial tissue can easily be discriminated from signal contributions from such extra-cardiac movements since the latter have a substantially identical impact on the respective sensor. Furthermore, by designing the sensors to be sensitive for certain frequency ranges, the majority of the extra-cardiac signal contributions may be omitted. Furthermore, band-pass filtering of the sensor outputs may also be used for discriminating or filter out the signal contribution from extra-cardiac movements.

Although modifications and changes may be suggested by those skilled in the art, it is the intention of the inventors to embody within the patent warranted heron all changes and modifications as reasonably and properly come within the scope of their contribution to the art.

We claim as our invention:

1. A system for monitoring cardiac synchrony in a human heart, said system comprising:
    a first sensor configured for positioning at a first location laterally relative to a cardiac wall of a heart that is subject to movements related to longitudinal valve plane movements of said cardiac wall along the longitudinal axis of the heart, said first sensor being configured to measure said cardiac wall movements at said first location at a first lateral distance from said cardiac wall and to emit a first sensor output signal corresponding thereto;
    a second sensor configured for positioning at a second location laterally relative to said cardiac wall of the heart that is subject to movements related to longitudinal valve plane movements along the longitudinal axis of the heart, said second sensor being configured to measure said movement of said cardiac wall movements at said second location at a second lateral distance from said cardiac wall, that is different from said first lateral distance, and to emit a second sensor output signal corresponding thereto;
    a lead arrangement electrically connected to said first and second sensors that conducts said first and second sensor output signals therefrom, respectively; and
    processing circuitry connected to said lead arrangement to receive said first and second sensor output signals therefrom, said processing circuitry being configured to process said first and second sensor output signals to produce a synchronization signal therefrom indicative of synchrony in the respective valve plane movements at said first and second cardiac wall locations.

2. A system as claimed in claim 1 wherein said first sensor is configured for placement at a first lateral distance from a ventricular wall, as said first cardiac wall location, and wherein said second sensor is configured for placement at a second lateral distance from the ventricular wall, as said second location.

3. A system as claimed in claim 2 wherein said first sensor is configured for placement at a wall of the right ventricle of the heart and said second sensor is configured for placement at a wall of the left ventricle of the heart, and wherein said processing circuitry is configured to generate an interventricular synchrony signal from said first and second sensor outputs, as said synchronization signal.

4. A system as claimed in claim 2 wherein said first and second sensors are configured for placement at the respective first and second locations of the same ventricle of the heart.

5. A system as claimed in claim 1 wherein at least one of said first and second sensors is configured for placement at an atrial wall, as said first or second location.

6. A system as claimed in claim 1 wherein said first and second sensors are configured for placement at first and second locations that are in proximity to said valve plane, at which said movements of said first and second locations are substantially longitudinal in correspondence with said movements of said valve plane.

7. A system as claimed in claim 1 comprising:
    a third sensor carried by said lead arrangement configured for placement at a third location that is subject to said movements related to said longitudinal valve plane movements along the longitudinal axis of the heart, said third sensor measuring said movements of said cardiac wall at said third cardiac wall location and emitting a third sensor output signal corresponding thereto; and
    said processing circuitry being configured to also receive and process said third output signal and to produce said synchronization signal from said first, second and third sensor output signals.

8. A system as claimed in claim 7 comprising:
    at least one further sensor carried by said lead arrangement and configured for placement at at least one further location that is subject to said movements related to said longitudinal valve plane movements, said at least one further sensor measuring said movements at said at least one further wall location and emitting at least one further sensor output signal corresponding thereto; and
    said processing circuitry being configured to also receive and process said at least one further sensor output signal and to produce said synchronization signal from said first, second, third and at least one further sensor output signals.

9. A system as claimed in claim 1 wherein said processing circuitry is configured to discriminate among respective signal contributions from longitudinal and lateral movements in said first and second sensor output signals.

10. A device as claimed in claim 1 wherein said processing circuitry is configured to compare said synchronization signal with a threshold signal and to emit an output indicative of whether cardiac synchrony is present.

11. A system as claimed in claim 1 wherein said processing circuitry is configured to process said first and second output signals by calculating a difference between said first and second output signals and to emit a difference signal, corresponding to said difference, as said synchronization signal.

12. A system as claimed in claim 1 wherein said processing circuitry is configured to process said first and second output signals by cross-correlating respective signal patterns of said first and second sensor output signals to obtain a cross-correlation result, and to emit said cross-correlation result as said synchronization signal.

13. A system as claimed in claim 1 wherein said processing circuitry comprises a neural network configured to process said first and second sensor output signals by neural network signal processing.

14. A system as claimed in claim 1 wherein said first and second sensors are accelerometers.

15. A system as claimed in claim 1 wherein said first and second sensors are piezoelectric pressure sensors.

16. A system as claimed in claim 1 wherein said first and second sensors are configured to measure, at said first and second wall locations, substantially only longitudinal movements.

17. A system as claimed in claim 1 comprising:
a housing configured for implantation in a subject, said housing containing said processing circuitry and having said lead arrangement mechanically and electrically connected thereto;
a pacing pulse generator contained in said housing that emits stimulation pulses for stimulating the heart;
control circuitry connected to said processing circuitry and to said pacing pulse generator and configured to control emission of said stimulation pulses by said pacing pulse generator dependent on said synchronization signal; and
at least one pacing electrode carried by said lead arrangement for delivering said stimulation pulses to cardiac tissue.

18. A system as claimed in claim 17 wherein said control circuitry is configured to change timing parameters associated with delivery of said stimulation pulses in dependence on said synchronization signal.

19. A system as claimed in claim 18 wherein said control circuitry is configured to change said timing parameters when said synchronization signal indicates an absence or reduction of cardiac synchrony.

20. A system as claimed in claim 19 wherein said control circuitry is configured to change said timing parameters to restore cardiac synchrony.

21. A system as claimed in claim 18 wherein said lead arrangement comprises a lead configured for placement in the right ventricle carrying an electrode for delivering some of said stimulation pulses to the right ventricle, and a lead configured for placement in the left ventricle carrying an electrode for delivering some of said stimulation pulses to the left ventricle, and wherein said control circuitry operates said pacing pulse stimulator in a biventricular pacing mode and wherein said timing parameters include a VV interval.

22. A system as claimed in claim 18 wherein said lead arrangement comprises a lead configured for placement in an atrium of the heart that carries an electrode for delivering some of said stimulation pulses to the atrium, and a lead configured for placement in a ventricle of the heart carrying an electrode for delivering some of said stimulation pulses to the ventricle, and wherein said control circuitry is configured to operate said pacing pulse generator in an AV pacing mode, and wherein said timing parameters include an AV interval.

23. A method for monitoring cardiac synchrony in a human heart, comprising the steps of:
positioning a first sensor at a first location laterally relative to a cardiac wall of a heart that is subject to movements related to longitudinal valve plane movements along the longitudinal axis of the heart and, with said first sensor, measuring said movements at said first location at a first lateral distance from said cardiac wall and emitting a first sensor output signal corresponding thereto;
positioning a second sensor at a second location laterally relative to the cardiac wall of the heart that is subject to movements related to longitudinal valve plane movements along the longitudinal axis of the heart and with said second sensor, measuring said movements of said cardiac wall at said second location at a second lateral distance from said cardiac wall, that is different from said first lateral distance, and emitting a second sensor output signal corresponding thereto; and
processing said first and second sensor output signals to produce a synchronization signal therefrom indicative of synchrony in the respective valve plane movements at said first and second locations.

24. A method as claimed in claim 23 comprising placing said first sensor at a first lateral distance from a ventricular wall, as said first location, and placing said second sensor at a second lateral distance from said ventricular wall, as said second location.

25. A method system as claimed in claim 24 comprising placing said first sensor at a wall of the right ventricle of the heart and placing said second sensor at a wall of the left ventricle of the heart, and generating an interventricular synchrony signal from said first and second sensor outputs, as said synchronization signal.

26. A method as claimed in claim 24 comprising placing said first and second sensors at the respective first and second, locations of the same ventricle of the heart.

27. A method system as claimed in claim 23 comprising placing at least one of said first and second sensors at an atrial wall, as said first or second location.

28. A method as claimed in claim 23 comprising placing said first and second sensors at first and second locations that are in proximity to said valve plane, at which said movements of said first and second locations are substantially longitudinal in correspondence with said movements of said valve plane.

29. A method as claimed in claim 23 comprising:
placing a third sensor at a third location that is subject to said movements related to said longitudinal valve plane movements along the longitudinal axis of the heart and, with said third sensor, measuring said cardiac wall movements at said third cardiac wall location and emitting a third sensor output corresponding thereto; and
also processing said third output signal to produce said synchronization signal from said first, second and third sensor output signals.

30. A method as claimed in claim 29 comprising:
placing at least one further sensor at at least one further location that is subject to said movements related to said longitudinal valve plane movements and, with said at least one further sensor, measuring said movements at said at least one further wall location and emitting at least one further sensor output signal corresponding thereto; and also processing said at least one further sensor output signal to produce said synchronization signal from said first, second, third and at least one further sensor output signals.

31. A method as claimed in claim 23 comprising, in said processing, discriminating among respective signal contributions from longitudinal and lateral movements in said first and second sensor output signals.

32. A method as claimed in claim 23 comprising comparing said synchronization signal with a threshold signal and to emit an output indicative of whether cardiac synchrony is present.

33. A method as claimed in claim 23 comprising processing said first and second output signals by calculating a difference between said first and second output signals and emitting a difference signal, corresponding to said difference, as said synchronization signal.

34. A method as claimed in claim 23 comprising processing said first and second output signals by cross-correlating respective signal patterns of said first and second sensor output signals to obtain a cross-correlation result, and emitting said cross-correlation result as said synchronization signal.

35. A method as claimed in claim 23 comprising processing said first and second sensor output signals by neural network signal processing.

36. A method as claimed in claim 23 comprising measuring, with said first and second sensors, substantially only longitudinal movements at said first and second wall locations.

37. A method as claimed in claim 23 comprising:
emitting stimulation pulses for stimulating the heart; and
controlling emission of said stimulation pulses dependent on said synchronization signal.

38. A method as claimed in claim 37 comprising controlling emission of said stimulation pulses by changing timing parameters associated with delivery of said stimulation pulses in dependence on said synchronization signal.

39. A method as claimed in claim 38 comprising changing said timing parameters when said synchronization signal indicates an absence or reduction of cardiac synchrony.

40. A method as claimed in claim 39 comprising changing said timing parameters to restore cardiac synchrony.

41. A system as claimed in claim 37 comprising delivering some of said stimulation pulses to the right ventricle of the heart, and delivering some of said stimulation pulses to the left ventricle of the heart in a biventricular pacing mode and wherein said timing parameters that are changed include a VV interval.

42. A system as claimed in claim 37 comprising delivering some of said stimulation pulses to an atrium of the heart, and delivering some of said stimulation pulses to a ventricle of the heart in an AV pacing mode, and wherein said timing parameters that are changed include an AV interval.

* * * * *